US008057421B2

(12) United States Patent
Akingba

(10) Patent No.: US 8,057,421 B2
(45) Date of Patent: Nov. 15, 2011

(54) MODULAR ARTERIO-VENOUS SHUNT DEVICE AND METHODS FOR ESTABLISHING HEMODIALYTIC ANGIOACCESS

(75) Inventor: Ajibola George Akingba, Huntington Woods, MI (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 570 days.

(21) Appl. No.: 12/189,669

(22) Filed: Aug. 11, 2008

(65) Prior Publication Data
US 2009/0062669 A1 Mar. 5, 2009

Related U.S. Application Data

(60) Provisional application No. 60/954,910, filed on Aug. 9, 2007.

(51) Int. Cl.
*A61M 5/00* (2006.01)
(52) U.S. Cl. .................................. 604/8; 604/9; 604/264
(58) Field of Classification Search .................. 604/8, 9, 604/507, 264
See application file for complete search history.

(56) References Cited

U.S. PATENT DOCUMENTS

| 4,397,335 | A | | 8/1983 | Doblar et al. | |
|---|---|---|---|---|---|
| 5,094,246 | A | | 3/1992 | Rusz et al. | |
| 6,663,590 | B2 | * | 12/2003 | Blatter | 604/103.01 |
| 7,025,741 | B2 | * | 4/2006 | Cull | 604/9 |
| 7,566,317 | B1 | * | 7/2009 | Batiste et al. | 604/9 |
| 2005/0038396 | A1 | * | 2/2005 | Claude et al. | 604/246 |
| 2005/0107733 | A1 | * | 5/2005 | Faul et al. | 604/8 |
| 2005/0119602 | A1 | | 6/2005 | Murphy et al. | |
| 2006/0190022 | A1 | | 8/2006 | Beyar et al. | |
| 2006/0224100 | A1 | * | 10/2006 | Gertner | 604/7 |

OTHER PUBLICATIONS

International Search Report issued in connection with PCT/US08/72828.

* cited by examiner

*Primary Examiner* — Leslie Deak
(74) *Attorney, Agent, or Firm* — Law Offices of Grady L. White, LLC

(57) ABSTRACT

The present invention provides an implantable modular AV shunt device, which is capable of monitoring and reporting its own patency, and which comprises a plurality of modular components that may be assembled and adjusted by the vascular surgeon during the implantation procedure, using well-known surgical techniques, in order to provide a custom fit and arrangement for the particular patient involved. The device comprises an arterial anastomotic valve that permits blood flowing through an artery to pass into the shunt device, a venous anastomotic valve that permits blood flowing through the shunt device to pass into a vein, a medial flow control unit, a first flexible shunt that carries blood from the arterial anastomotic valve to the medial flow control unit, a second flexible shunt that carries blood from the medial flow control unit to the venous anastomotic valve, and a valve control system. The valve control system is operable to control both the rate at which blood is permitted to enter the shunt device via the arterial anastomotic valve, as well as the rate at which blood is permitted to exit the shunt device via the venous anastomotic valve.

40 Claims, 7 Drawing Sheets

FIG. 4A – Closed Position
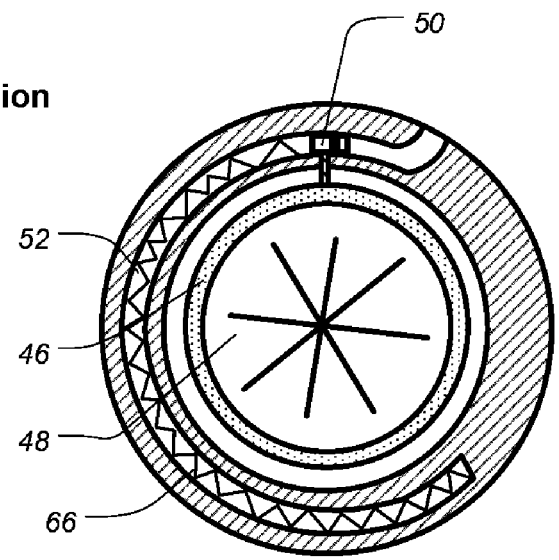
FIG. 4B – Half Open Position
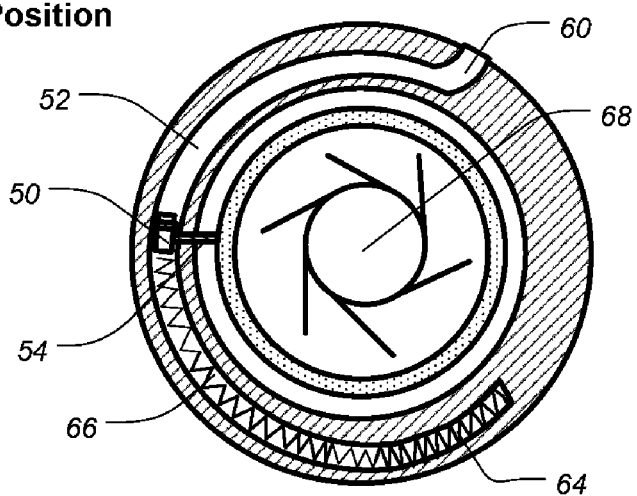
FIG. 4C – Fully Open Position
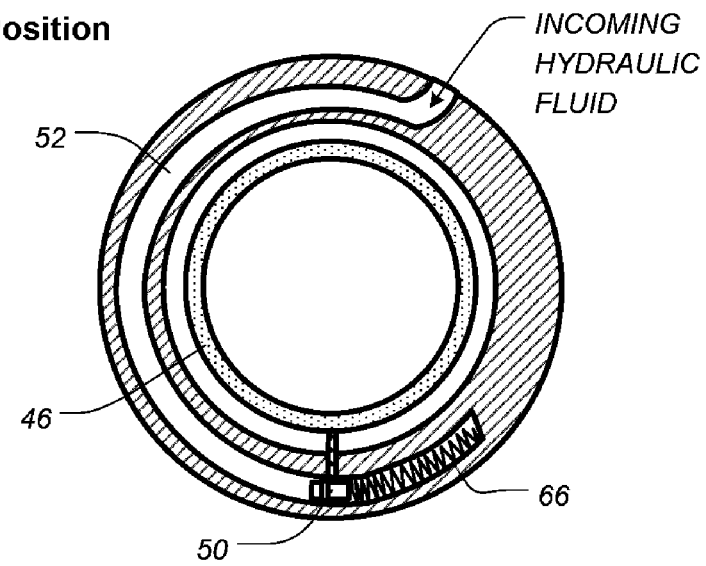

MODULAR ARTERIO-VENOUS SHUNT DEVICE AND METHODS FOR ESTABLISHING HEMODIALYTIC ANGIOACCESS

CROSS-REFERENCE TO RELATED APPLICATIONS

This application is related to and claims priority under 35 U.S.C. §119 to provisional application No. 60/954,910, filed on Aug. 9, 2007, which is incorporated into this application in its entirety by this reference.

FIELD OF ART

The present invention relates generally to devices and methods for performing hemodialysis for patients suffering from end-stage renal disease (ESRD). More particularly, the invention provides an implantable modular arteriovenous shunt system and methods of using same for establishing hemodialytic angioaccess.

RELATED ART

Hemodialysis is a method of removing waste products, such as potassium and urea, as well as free water, from the blood when the kidneys are incapable of adequately performing this function on their own (a condition known as end-stage renal failure). In a typical hemodialysis session, two hypodermic needles are inserted into the patient's body. One needle draws untreated blood from the patient's vascular system and conveys it to an extracorporeal hemodialysis machine for cleansing, while the second needle carries the treated blood from the hemodialysis machine back into the patient's vascular system. For some hemodialysis patients, it may be necessary to undergo these sessions three or more times per week until the failing kidney(s) can be repaired or replaced, or sometimes for the rest of the patient's life. Over time, repeated insertion and removal of needles into the patient's arteries and veins weaken the vessel walls and produce a significant risk of developing infections and aneurysms (large bulges in the vessel walls).

To mitigate or avoid these risks, current practices for providing hemodialysis treatment include implanting a synthetic arteriovenous fistula or synthetic arteriovenous graft, also called an "AV shunt." An AV shunt is an artificial vessel used to join an artery to a vein in such a way that blood flows out of an artery, through the shunt and then back into a vein. Although the AV shunt is implanted below the surface of the skin, hemodialysis technicians gain access to the blood flowing through the AV shunt by piercing the skin and the AV shunt with the hypodermic needles, instead of piercing the patient's natural arteries and veins. Thus, untreated blood flowing from a patient's artery into the AV shunt is drawn out of the AV shunt via one hypodermic needle inserted near the arterial end of the AV shunt, and the treated blood is returned to the body via another hypodermic needle that is inserted near the venous end of the AV shunt. As the cleansed blood flowing from the hemodialysis machine is returned to the venous end of the AV shunt via the second hyperdermic needle, it flows into the patient's vein, which carries the blood back into the patient's general circulatory system. The advantage of using an AV shunt is that it avoids, or at least reduces, the trauma and damage that would otherwise occur to the patient's natural blood vessels. Depending on the length of the AV shunt, it also provides a larger surface area for accessing the flow of blood, which permits hemodialysis techni- cians to pierce the patient's body using a more dispersed insertion pattern, thereby reducing the risk and incidence of infection and scarring of the dermal and epidermal layers of the patient's skin.

Unfortunately, there are a number of problems associated with using conventional AV shunts. It has been observed, for example, that implantable AV shunts often fail. Pathological study of the proximal veins of failed AV shunts has revealed a large incidence of myointimal hyperplasia secondary to vessel injury from turbulence, compliance mismatch between graft material and vein, and mechanical stimulation of perivascular tissues at the anastomosis graft and vessel. Normal blood flow is laminar, with the cellular elements flowing centrally in the vessel lumen, separated from the endothelium by a slower moving clear zone of plasma. Turbulence and stasis caused by the blood flowing into the vein from the AV shunt contribute to clot formation by disrupting laminar flow and bringing platelets into contact with the endothelium, preventing dilution of activated clotting factors from fresh flowing blood, retarding the inflow of clotting factor inhibitors (thus permitting the build up of thrombi) and promoting endothelial cell activation. This situation predisposes the patient to local thrombosis, leukocyte adhesion, and a variety of other endothelial cell effects. Other reasons for shunt failure include recurrent shunt stenosis, infection, pseudoaneurysms and steal syndrome.

When complications associated with implanted AV shunts, such as myointimal hyperplasia, thrombosis, shunt stenosis and clotting, arise and go undetected for a significant period of time, the AV shunt can fail without warning, resulting in potentially devastating consequences. These complications may sometimes be detected in a medical facility while the patient is undergoing dialysis or being treated or examined by a medical professional. The complications also might be detected while the patient is hooked up to complicated and expensive external medical machines and equipment that are designed to monitor and/or test the patient for signs of complications. Prior to the present invention, however, there has been no AV shunt device introduced that has the capacity to monitor and report its own patency data. Consequently, the frequency and unpredictable timing of AV shunt failures and the emergency salvage procedures required to restore their patency (e.g., thrombectomy, angioplasty or revision) presents enormous health, safety and logistical challenges for the patient, surgeon, operating room and dialysis centers.

Another significant problem associated with existing implantable AV shunts is that they cannot easily be adjusted (i.e., shortened or extended) by the vascular surgeon during the implantation procedure to provide the optimum fit and arrangement for a patient based on that particular patient's physical anatomy and condition. Implantable AV shunts are typically implanted in the leg or arm of the patient, which means the size, geometry, condition and availability of an implantation site on a patient that is very tall, muscular, large and/or overweight will be considerably different from the size, geometry and availability of an implantation site on a patient that is very short, lacking in muscular development, undersized and/or underweight. Similarly, the physical condition of the implantation site on a patient that has already been subjected to frequent and/or long term hemodialysis treatments will be very different from the physical condition of the same implantation site on a patient with little or no history of such treatments. Numerous variations in age, mobility and general health of hemodialysis patients also produce numerous variations in respect to the size, geometry, condition and availability of proposed implantation sites.

Vascular surgeons have attempted to deal with these variations and address unexpected problems arising during surgery by having a number of AV shunts of different sizes on hand before surgery begins. However, because the number and range of physical characteristics and considerations that may determine the optimum site, size and arrangement of the implanted AV shunt is almost unlimited, and because some of these characteristics and considerations may not be known or fully appreciated before surgery begins, it is frequently the case that none of the AV shunts available to the surgeon during the implantation procedure provides the optimal fit and arrangement for the particular patient or implantation site. In these situations, surgeons often have no choice but to use an AV shunt having a size that is less than optimal for the particular patient, and or use an arrangement or configuration for the shunts that is less than optimal.

For example, U.S. Pat. No. 7,025,741 issued to Cull, which is hereby incorporated herein in its entirety by this reference, discloses an implantable arteriovenous graft system that the inventor claims eliminates or at least reduces arterial steal and thrombosis by providing an arteriovenous graft (shunt) having at one or both ends a valve device comprising an inflatable balloon or a magnetically-activated piston which, when activated, constricts the graft to partially or entirely prevent the flow of blood while the patient is not undergoing dialysis treatment. In order to determine whether the device is effective in eliminating or reducing arterial steal, however, Cull suggests monitoring the patient's condition over a period of time, such as days or weeks, while selectively opening and closing the valve until arterial steal is minimized. Thus, Cull's device has no ability to monitor itself, or to store and report its own patency data (e.g., flow data near the arterial end of the graft indicating the existence of arterial steal), which may increase the risk that arterial steal might go undetected for a longer period of time. As a result, the patient must be monitored for symptoms of arterial steal. Moreover, because Cull's device comprises a single graft (shunt) with valves at one or both ends, a vascular surgeon using Cull's device has little or no ability during surgery to shorten the overall length of the device (e.g., by cutting pieces off one or both ends of the graft) or extending the overall length of the device (e.g., by inserting additional or longer pieces of graft material between the valves) in order to construct a device that has the optimal overall length for the particular patient and/or implantation site.

Accordingly, there is a need for an implantable AV shunt device capable of monitoring and storing data concerning its own patency, even when the patient is not at a medical facility, and further capable of transmitting the stored patency data to an external medical device and/or technician for further processing and analysis upon demand. There also is a need for an implantable AV shunt device that may be adjusted and/or resized by the vascular surgeon during the implantation procedure to provide a custom fit for the patient, regardless of the patient's size or the geometry of the implantation site, using surgical techniques that most vascular surgeons are already very familiar and comfortable with.

SUMMARY OF INVENTION

The present invention addresses these needs by providing an implantable modular AV shunt device, which is capable of monitoring and reporting its own patency, and which comprises a plurality of modular components that may be assembled and adjusted by the vascular surgeon during the implantation procedure, using well-known surgical techniques, in order to provide a custom fit and arrangement. The device comprises an arterial anastomotic valve that permits blood flowing through an artery to pass into the shunt device, a venous anastomotic valve that permits blood flowing through the shunt device to pass into a vein, a medial flow control unit, a first flexible shunt that carries blood from the arterial anastomotic valve to the medial flow control unit, a second flexible shunt that carries blood from the medial flow control unit to the venous anastomotic valve, and a valve control system that may be activated to control the rate at which blood is permitted to enter the shunt device via the arterial anastomotic valve, as well as the rate at which blood is permitted to exit the shunt device via the venous anastomotic valve.

More particularly, the valve control systems operates to control the diameter of iris-like apertures in the valves, which apertures are formed by the walls of cylindrically-shaped sleeves fixedly attached to static and rotating rings located in the arterial and venous anastomotic valves. When a dialysis treatment is to begin, the valve control system is activated to cause the diameter of the apertures to expand, thereby permitting blood to flow from the artery into and through the arterial anastomotic valve, through the first flexible shunt interposed between the arterial anastomotic valve and the medial flow control unit, through the medial flow control unit, through the second flexible shunt interposed between the medial flow control unit and the venous anastomotic valve, into the venous anastomotic valve, and then out of the device and into the vein. Hypodermic needles, which are attached to the dialysis machine, are inserted into the first and second flexible shunts in order to draw blood out of the modular shunt device for cleansing and to return the cleansed blood to the patient's vascular system. When the dialysis treatment is finished and the hypodermic needles are removed from the first and second flexible shunts, the valve control system is activated again to contract the diameter of the apertures, thereby preventing blood from continuing to flow into the modular shunt device. Biasing means within the valves keep the valves closed until it is time for the next dialysis session, whereupon the valve control system is reactivated to open and close the valves again.

Embodiments of the present invention include an integrated surveillance system configured to collect data representing quantitative measurements for the flow of blood through the vessels in the vicinity of the arterial and venous anastomotic valves. More specifically, the arterial and venous anastomotic valves are equipped with one or more flow sensors that are electrically coupled to a microprocessor in the medial flow control unit. Electrical leads, which are preferably embedded in the flexible flow tubes, provide the electrical conduits for conveying the electrical signals from the flow sensors to the medial flow control unit, and these electrical signals represent the values of the quantitative blood flow measurements. As discussed in more below, the medial flow control unit houses a printed circuit board containing the microprocessor, as well as one or more memory modules, transceivers and batteries, all of which cooperate to collect, store and wirelessly transmit the measured blood flow data to an external receiver for further processing and analysis by other medical devices and technicians.

In another aspect of the invention, there is provided a method for establishing hemodialytic angioacess, comprising (1) attaching an arterial anastomotic valve to an artery, the arterial anastomotic valve comprising a first static ring, a first rotating ring, and an arterial aperture formed by a first sleeve interposed between the first static ring and the first rotating ring; (2) attaching a venous anastomotic valve to a vein, the venous anastomotic valve comprising a second static ring, a second rotating ring, and a venous aperture formed by a second sleeve interposed between the second static ring and the second rotating ring; (3) providing a medial flow control unit; (4) installing a first flexible shunt between the medial flow control unit and the arterial anastomotic valve; (5) installing a second flexible shunt between the medial flow control unit and the venous anastomotic valve; and (5) rotating the first and second rotating rings in a first direction to cause the first and second sleeves to untwist, thereby expanding the arterial and venous apertures to increase the rate at which blood is permitted to flow through the arterial and venous anastomotic valves. The method may further include: (6) rotating the first and second rotating rings in the opposite direction to cause the first and second sleeves to twist, thereby contracting the arterial and venous apertures to reduce the rate at which blood is permitted to flow through the arterial and venous anastomotic valves. Typically, rotating the first and second rotating rings is accomplished by injecting hydraulic fluid into a fluid injection port attached to the medial flow control unit, thereby forcing the hydraulic fluid into the first and second hydraulic fluid tubes and the arterial and venous anastomotic valves, which in turn forces the first and second rotating rings to rotate in the direction that expands the arterial and venous apertures to permit a higher rate of flow.

BRIEF DESCRIPTION OF THE DRAWINGS

The present invention and various aspects, features and advantages thereof are explained in detail below with reference to exemplary and therefore non-limiting embodiments and with the aid of the drawings, which constitute a part of this specification and include depictions of the exemplary embodiments. In these drawings:

FIGS. 4A, 4B, and 4C show, respectively, cross-sectional views of the venous anastomotic valve in the closed, half open and fully-open positions.

DETAILED DESCRIPTION OF EXEMPLARY EMBODIMENTS

Figure 1:
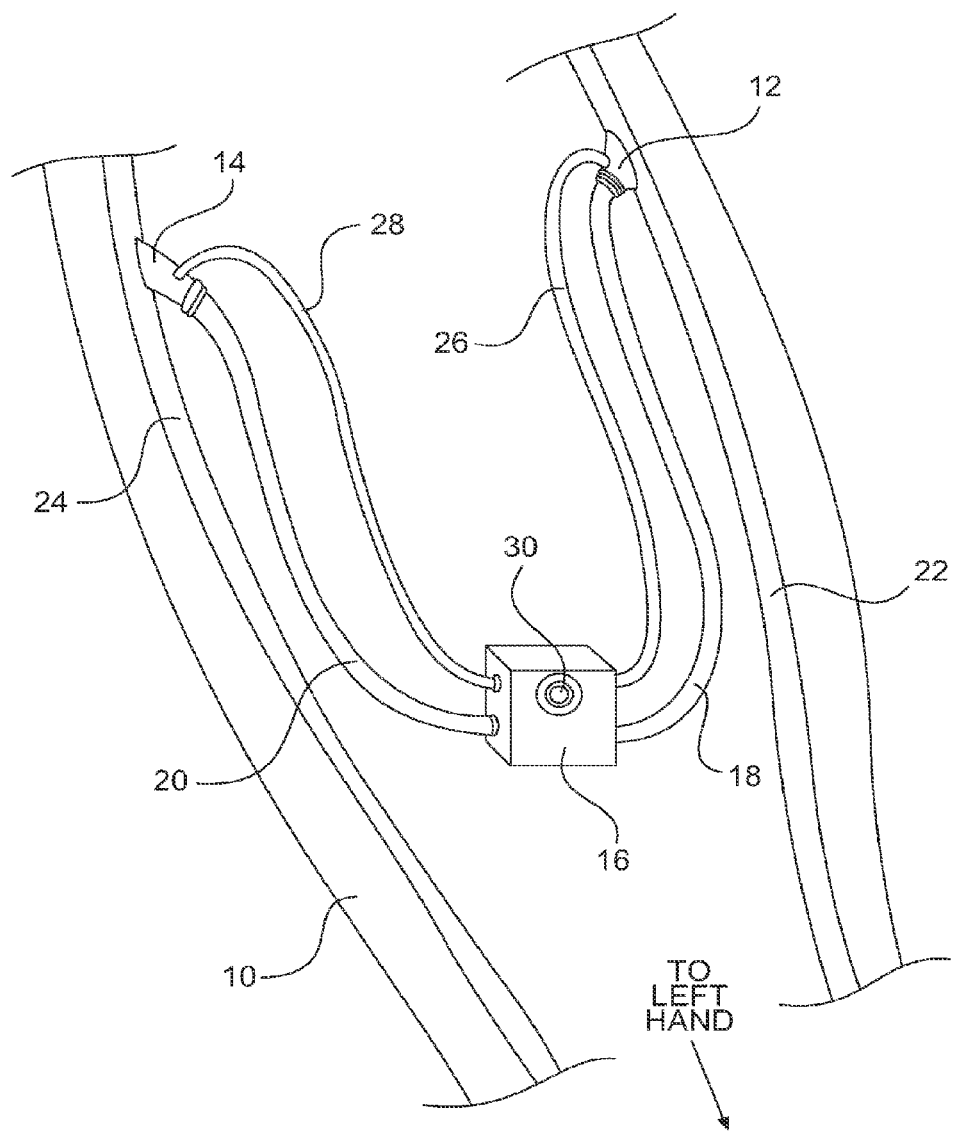
FIG. 1 shows an exemplary embodiment of a modular arteriovenous shunt device according to the present invention.

The present invention provides an arteriovenous shunt device for establishing hemodialytic angioacess. Devices operating according to a preferred embodiment of the present invention are capable of collecting and storing data concerning its own patency, and transmitting the data to an external receiver for further processing and analysis by medical technicians or practitioners. While prior art devices typically require that the vascular surgeon install a single flexible shunt having a fixed length between the artery and the vein, the present invention has a modular design that includes at least two flexible shunts and one medial flow control unit. The medial flow control unit, which houses the microprocessor, a memory storage device, a transceiver and a battery, is relatively easily connected between the two flexible shunts by the vascular surgeon during the implantation procedure. Because the device comprises at least three conjoined pieces instead of one, vascular surgeons have greater flexibility when it is determined during implantation and repair surgery that the overall length and/or arrangement of the shunt device needs to be shortened, extended and/or modified in order to accommodate the specific physical characteristics or conditions of the implantation site. With the present invention, for example, the vascular surgeon can easily cut one or both of the flexible shunts at the ends abutting the medial flow control unit during surgery in order to produce a shunt device having a shorter overall length. The surgeon may also decide during surgery, depending on the circumstances and desired arrangement of the shunt device under the patient's skin, to use two flexible shunts having lengths that are substantially different from each other. Another advantage of the present invention is that, when one of its components fails, begins to deteriorate or simply needs replacing due to age or the availability of technical upgrades, that component may easily be removed and replaced by the vascular surgeon without removing and replacing the entire shunt device.

Preferred embodiments of the invention include an arterial anastomotic valve, a venous anastomotic valve, one or more flow sensors attached to one or both of the anastomotic valves, a medial flow control unit, two flexible shunts and a valve control system. The arterial anastomotic valve is surgically connected to an artery in the patient's arm or leg and is configured to permit blood flowing through that artery to pass into the shunt device when the valve is in the open position. The venous anastomotic valve is surgically connected to a nearby vein in the patient's arm or leg, and is configured to permit blood flowing through the shunt device to pass into the patient's vein when the valve is in the open position. The first flexible shunt, which is connected at one end to the arterial anastomotic valve and connected at its other end to the medial flow control unit, carries blood from the arterial anastomotic valve to the medial flow control unit. The second flexible shunt, which is connected at one end to the medial flow control unit and connected at its other end to the venous anastomotic valve, carries blood from the medial flow control unit to the venous anastomotic valve. During a dialysis session, both the arterial anastomotic valve and the venous anastomotic valves or opened to permit blood to flow through the two flexible shunts and the medial flow control unit, and two hypodermic needles, which are fluidly connected to the dialysis machine, are inserted into the two flexible shunts in order to carry blood from the arterial end of the shunt device into the dialysis machine for cleansing and to carry the cleansed blood from the dialysis machine back to the venous end of the shunt device.

The arterial anastomotic valve comprises a static ring, a rotating ring, and an arterial aperture formed by a cylindrically-shaped sleeve fixedly attached at one end to the first static ring and fixedly connected at its other end to the rotating ring. The venous anastomotic valve comprises a second static ring, a second rotating ring, and a venous aperture formed by a second cylindrically-shaped sleeve fixedly attached at one end to the second static ring and and fixed connected at its other end to the second rotating ring. When the valve control system is activated to open the valves, the first and second rotating rings in the valves rotate in one direction (although not necessarily in the same direction), which causes the first and second cylindrical sleeves to untwist, thereby expanding the diameter of the arterial and venous apertures and increasing the rate blood is permitted to flow through those apertures. When the valve control system is activated to close the valves, the first and second rotating rings rotate in the opposite direction, which causes the first and second cylindrical sleeves to twist together, thereby contracting the arterial and venous apertures to reduce the rate at which blood is permitted to flow through the valves. When the patient is not undergoing dialysis treatment, the arterial and venous apertures are preferably sufficiently contracted to entirely prevent blood from flowing into or through the shunt device.

In preferred embodiments, the valve control system uses flexible fluid tubes, hydraulic fluid, fluid-filled chambers, and a biasing means (such as a spiral spring, a gas spring, a compressible foam or a compressible fluid) to force the rotating rings in the anastomotic valves to rotate in a manner that causes the cylindrically-shaped sleeves to untwist and twist, thereby forming iris-like apertures that open and close to permit or prevent the flow of blood into and out of the shunt devices. Thus, as will be described in more detail below, components of the valve control system may be located inside and between some of the other components of the device, such as the arterial anastomotic valve, the venous anastomotic valve and the medial flow control unit.

In particular, the valve control system in preferred embodiments comprises a first spiral chamber disposed about the circumference of the arterial anastomotic valve, the first spiral chamber having an open end, a closed end and a slot running along its interior-facing side. A plunger, which is slidably enclosed in the first spiral chamber, is biased toward the open end of the first spiral chamber by a spiral or helical spring or some other suitable biasing means. A rod having one end connected to the plunger and the other end connected to a fixed position on the perimeter of the first rotating ring passes through the slot so that movement of the plunger through the spiral chamber caused by pressure exerted by the hydraulic fluid or the biasing means causes the first rotating ring to rotate in the same direction as the plunger's movement, thereby opening or closing the aperture formed by the walls of the twisting and untwisting cylindrical sleeve attached to the first rotating ring.

The open end of the first spiral chamber is in fluid communication with a first flexible fluid tube whose other end is fluidly coupled to a bibb on the medial flow control unit. This flexible fluid tube may or may not be at least partially filled with hydraulic fluid at all times, even when the valve control system is not currently in use. The bibb on the medial flow control unit is fluidly coupled to a fluid injection port attached to the medial flow control unit. When a dialysis session is about to begin, additional hydraulic fluid is injected into the fluid injection port (this may be accomplished, for example, with a hypodermic needle filled with hydraulic fluid), which causes the hydraulic fluid already inside the first flexible fluid tube, as well as some of the injected hydraulic fluid, to pass from the first flexible fluid tube into the first spiral chamber. The increased pressure exerted by the additional hydraulic fluid forces the plunger in the first spiral chamber to overcome the pressure exerted by biasing means and to move toward the closed end of first spiral chamber. As previously stated, because the plunger is fixedly connected to the perimeter of the first rotating ring, the plunger's movement through the first spiral chamber causes the first rotating ring to rotate, which untwists the walls of the twisted cylindrical sleeve, thereby expanding the arterial aperture to permit blood to flow into and through the shunt device.

When a dialysis session is finished, hydraulic fluid is extracted from the fluid injection port, which causes the hydraulic fluid previously forced into the first spiral chamber to evacuate the first spiral chamber through the first flexible fluid tube, and permits the biasing means to force the plunger back toward the open end of the first spiral chamber. As the plunger moves back toward the open end of the spiral chamber, it pulls on the perimeter of the first rotating ring, which causes the first rotating ring to rotate in the opposite direction to contract the arterial aperture and gradually reduce and eventually prevent the flow of blood into the shunt device.

The components of the valve control system which are located in or connected to the arterial anastomotic valve, as described above, are substantially duplicated at the venous end of the shunt device so that the opening and closing of the iris-like aperture in the venous anastomotic valve (in order to permit or prevent blood to flow out of the device and into the patient's vascular system) may be accomplished and controlled in substantially the same manner. Thus, the valve control system further comprises a second spiral chamber disposed about the circumference of the venous anastomotic valve, which second spiral chamber has a second open end, a second closed end and a second slot running along its interior-facing side. A second plunger, which is slidably enclosed in the second spiral chamber, is biased toward the second open end by a second biasing means (such as a second spiral spring). There is also a second rod extending through the second slot, the second rod having one end connected to the second plunger and the other end connected to a fixed position on the perimeter of the second rotating ring, so that when the second plunger moves back and forth through the second spiral chamber, the movement causes the second rotating ring to rotate, thereby untwisting and twisting the walls of the second cylindrically-shaped sleeve to open and close the venous aperture to permit or prevent the flow of blood through that aperture.

A second flexible fluid tube is provided, which is in fluid communication with both the fluid injection port attached to the medial flow control unit and the second open end of the second spiral chamber. The second flexible fluid tube may also be at least partially filled with hydraulic fluid. Therefore, when the dialysis session is about to begin and the additional hydraulic fluid is injected into the fluid injection port attached to the medial flow control unit, at least some of the additional hydraulic fluid forces the hydraulic fluid already inside said second flexible fluid tube to pass into the second spiral chamber, thereby forcing the second plunger to move against the second biasing means toward the closed end of the second spiral chamber. The movement of the second plunger causes the second rotating ring to rotate in one direction, thereby causing the venous aperture to expand, which permits blood to flow out of the venous anastomotic valve into the patient's vein. Conversely, when the dialysis session is completed and the additional hydraulic fluid is extracted from the fluid injection port, this causes the hydraulic fluid previously forced into the second spiral chamber to evacuate the second spiral chamber, which permits the second biasing means to force the second plunger back toward the open end of the second spiral chamber, thereby causing the second rotating ring to rotate in the opposite direction to contract the venous aperture and reduce or prevent blood from flowing out of the shunt device into the patient's vein.

Embodiments of the present invention may also include one or more venous flow sensors attached to the venous anastomotic valve, which are configured to record data describing the flow of blood in the vicinity of the venous anastomotic valve and to transmit the data to the medial flow control unit via an electrical lead that electrically couples the venous flow sensors to the medial flow control unit. In preferred embodiments, the electrical lead is embedded in the flexible fluid tube carrying the hydraulic fluid used to open and close the venous valve. The venous flow sensors may comprise any type of biocompatible fluid sensors suitable for measuring the flow of fluid, including, for example, a hot-wire anemometer configured to measure the forced convective heat transfer from a thermal element to the blood. The purpose of the venous flow sensors is take and record quantitative measurements of the blood flow in and around the area where the venous anastomotic valve joins with the vein, and thereby help to detect conditions such as increased or extraordinary turbulence that may lead to thrombosis and aneurysms.

The medial flow control unit interposed between the two flexible shunts and two flexible fluid tubes includes a microprocessor, a memory storage device, a transceiver and a battery. As the data recorded by the venous flow sensor is transmitted to the medial flow control unit via the electrical lead embedded in the flexible fluid tube, the microprocessor is configured to store the received data in the memory storage device. The transceiver, which is coupled to the microprocessor, is configured to receive a predetermined radio frequency signal generated by an external transmitter and pass that signal to the microprocessor. When the microprocessor receives the predetermined radio frequency signal, it is programmed to retrieve the data stored in the memory storage device and cause the transceiver to wirelessly transmit the retrieved data to an external receiver using, for example, another predetermined radio frequency signal. The battery acts as a power source for the microprocessor, transceiver and memory storage device.

Embodiments of the present invention may also include one or more arterial flow sensors, attached to the arterial anastomotic valve, which are configured to record data describing the flow of blood through the artery in the vicinity where the artery joins with the arterial anastomotic valve and transmit that data to the medial flow control unit for storage in the memory storage device. The data are transmitted to the medial flow control unit via a second electrical lead embedded in the flexible fluid tube interposed between the arterial anastomotic valve and the medial flow control unit. These data may be helpful in detecting arterial steal syndrome. Notably, the venous and arterial flow sensors and the microprocessor are configured to record and store blood flow data regardless of whether the patient is currently undergoing dialysis treatment. Therefore, the blood flow data collection and storage functions continue to be carried out even when the patient is away from medical technicians and medical facilities.

Turning now to the drawings, FIG. 1 shows an exemplary embodiment of a modular arteriovenous shunt device, according to the present invention, when it is subcutaneously implanted in a patient's left forearm 10. As shown in FIG. 1, the modular arteriovenous shunt device includes an arterial anastomotic valve 12, a venous anastomotic valve 14, a medial flow control unit 16, a first flexible shunt 18, and a second flexible shunt 20. The arterial anastomotic valve 12 is surgically attached to the wall of the patient's artery 22 in such a way that when arterial anastomotic valve 12 is in the open position, at least some portion of the blood flowing through the artery 22 is permitted to pass into and through arterial anastomotic valve 12 and first flexible shunt 18. First flexible shunt 18 carries the blood from arterial anastomotic valve 12 to medial flow control unit 16. The venous anastomotic valve 14 is surgically attached to vein 24 in such a way that, when the venous anastomotic valve 14 is in the open position, blood flowing from the medial flow control unit 16 is permitted to pass into and through second flexible shunt 20, where it then passes into and through venous anastomotic valve 14 before being emptied into the patient's vein 24.

A hypodermic needle (not shown in FIG. 1) fluidly coupled to an external dialysis machine (also not shown in FIG. 1) may be inserted into first flexible shunt 18 anywhere along its length in order to channel some of the blood flowing through first flexible shunt 18 out of the shunt device and into the dialysis machine for cleansing. Any blood flowing through first flexible shunt 18 that does not exit the shunt device via the hypodermic needle inserted into first flexible shunt 18 continues to flow toward and through the medial flow control unit 16, through the second flexible shunt 20, through the venous anastomotic valve 14 and finally into the patient's vein 24. A second hypodermic needle (not shown in FIG. 1) fluidly coupled to the dialysis machine is inserted into the second flexible shunt 20 anywhere along its length. The second hypodermic needle carries cleansed blood from the dialysis machine to the second flexible shunt 20, whereupon the cleansed blood is mixed with any blood that has flowed through medial flow control unit 16 and then returned to the patient's body via venous anastomotic valve 14 and patient vein 24.

As shown in FIG. 1, the modular arteriovenous shunt device also includes a first flexible fluid tube 26 that fluidly couples medial flow control unit 16 to arterial anastomotic valve 12. A second flexible fluid tube 28 fluidly couples medial flow control unit 16 to venous anastomotic valve 14. As will be discussed in more detail below, first flexible fluid tube 26 and second flexible fluid tube 28 are also fluidly coupled to a fluid injection port 30 attached to medial flow control unit 16, which provides a mechanism for introducing hydraulic fluid into the device and extracting hydraulic fluid from the device in order to control the opening and closing of the apertures in arterial anastomotic valve 12 and venous anastomotic valve 14.

First flexible shunt 18, second flexible shunt 20, first flexible fluid tube 26 and second flexible fluid tube 28 are typically manufactured from polytetrafluoroethylene (PTFE). However, any other biocompatible material may be used without departing from the scope of the claimed invention. Preferably, but not necessarily, the flexible shunts have a diameter that is roughly equivalent to the diameter of the arterial and venous anastomotic valves. The flexible fluid tubes may have diameters somewhat larger or smaller than the diameters of the flexible shunts, depending, for example, on the volume of hydraulic fluid and the pressure required to smoothly operate the anastomotic valves.

Figure 2:
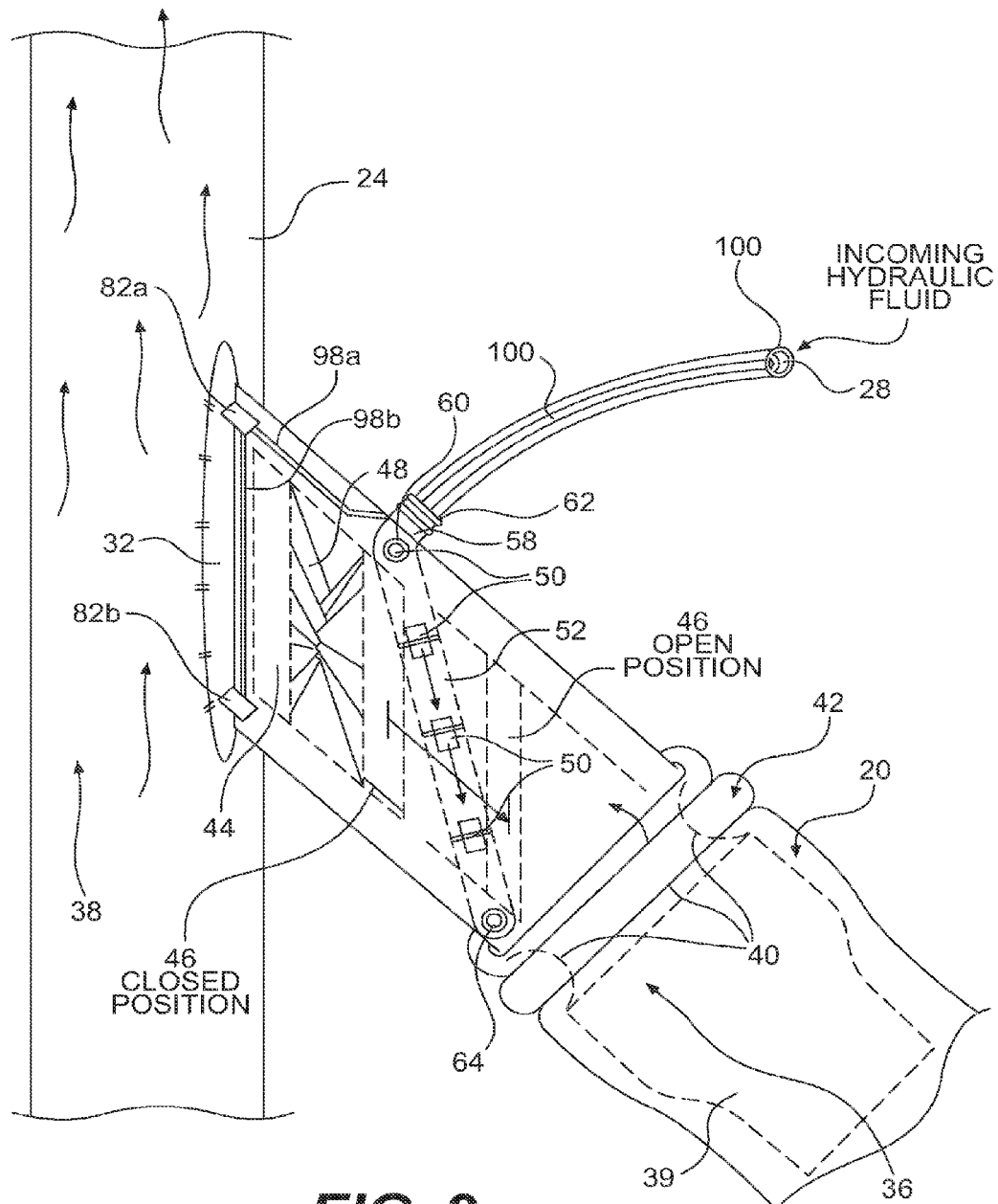
FIG. 2 provides a more detailed view of a venous anastomotic valve according to one embodiment of the invention.

FIG. 2 provides a more detailed view of venous anastomotic valve 14 according to one embodiment of the invention. As shown in FIG. 2, one end of venous anastomotic valve 14 includes a flange 32, which is sutured to the vein 24 (or artery in the case of an arterial anastomotic valve) when the device is implanted in a patient. The flanged end of the venous anastomotic valve 14 is also beveled in order to facilitate attaching the venouos anastomotic valve 14 to the vein 24 at an angle of less than ninety degrees, which reduces the amount of turbulence that might otherwise occur as blood 36 flowing through the device and venous anastomotic valve 14 collides with blood 38 already moving through vein 24.

The other end of venous anastomotic valve 14 (i.e., the end connected to second flexible shunt 20) is somewhat tapered so that it will fit easily, but snugly, into the open end of second flexible shunt 20. The tapered end 39 of the venous anastomotic valve 14 also contains an annular-shaped notch 40, which provides a stable and secure resting position for a clamp or rubber band 42 that may be used to fasten second flexible shunt 20 onto the tapered end 39 of venous anastomotic valve 14 during the implantation procedure and hold second flexible shunt 20 in place thereafter. The tapered end 39 of venous anastomotic valve 14 may alternatively contain ridges and/or protrusions (not shown in FIG. 2) on or about its outer surface to provide a stable and secure resting coupling between venous anastomotic valve 14 and second flexible shunt 20. As shown in FIG. 2, for example, the second flexible shunt 20 is fastened to the venous anastomotic valve 14 by pushing the second flexible shunt 20 past an annular notch 40 carved into the tapered end 39 of the venous anastomotic valve 14 and then seating rubber band 42 on top of the second flexible shunt 20 so that the rubber band 42 is firmly seated in the notch 40 and the second flexible shunt 20 is firmly compressed by the rubber band 42 against the outer walls of the tapered end 39. Thus, fastening the flexible shunts to the anastomotic valves is relatively straight forward, does not require special tools or surgical instruments, and can easily be accomplished by the vascular surgeon during the implantation procedure, even if it becomes necessary to cut away a portion of the flexible shunt before it is attached.

Inside venous anastomotic valve 14 there is an iris valve-like structure comprising a static ring 44, a rotating ring 46 and an aperture formed by the twisting walls of a cylindrically-shaped sleeve 48 having one end that is fixedly attached to the static ring 44 and an opposite end that is fixedly attached to the rotating ring 46. The static ring 44 is preferably located as close as possible to the beveled and flanged end of the venous anastomotic valve 14, while the rotating ring 46 is located closer to (but not necessarily adjacent to) the tapered end 39. When the shunt device is first implanted and dialysis is not occurring, the rotating ring 46 is positioned so that the wall of the sleeve 48 is twisted, causing the segments of the wall to fold over each other in a helical arrangement. This position causes the aperture formed by the walls of the sleeve 48 to contract and form a barrier through which the blood 36 cannot flow. The position for the rotating ring 46 while the aperture is closed in this manner is indicated in FIG. 2 with the label "46 Closed Position."

When a hemodialysis session is about to begin, the rotating ring 46 is rotated approximately 180 degrees from its closed position so that wall segments of the sleeve 48 untwist and unfold, thereby expanding the aperture formed by the walls of sleeve 48 into a cylindrically-shaped open passageway through which the blood 36 is permitted to flow. As the rotating ring 46 rotates to untwist the sleeve 48 and open the passageway, it also changes its vertical and horizontal position within the venous anastomotic valve 14, moving further away from the static ring 44 (i.e., down and to the right in FIG. 2) and coming to rest in the position indicated in FIG. 2 with the reference "46 Open Position."

When both the arterial anastomotic valve 12 and the venous anastomotic valve 14 are open, the device permits blood to flow out of the artery 22, into and through the arterial anastomotic valve 12, through the first flexible shunt 18, through the medial flow control unit 16, through the second flexible shunt 20, through the venous anastomotic valve 14 and finally into the vein 24. While this is occurring, hypodermic needles may be inserted into one or both of the flexible shunts in order to extract blood from and return blood to the patient's vascular system.

After the hemodialysis session is completed, the rotating ring 46 is rotated about 180 degrees in the opposite direction, which causes the walls of the sleeve 48 to twist and fold over each other again, thereby contracting the diameter of the aperture to cut off the flow of blood 36. Closing the aperture also causes the rotating ring 46 to travel toward the static ring 44 again (i.e., up and to the left in FIG. 2) and comes to rest in its initial position. The vertical and horizontal travel of the rotating ring as it opens and closes may be guided and supported by notches and/or grooves (not shown in FIG. 2) along the interior wall surfaces of the venous anastomotic valve 14.

Valve Control System

In the embodiment of the invention shown in FIGS. 1 and 2, the opening and closing of the venous anastomotic valve 14 and arterial anastomotic valve 12 (and, more particularly, the rotation of the rotating rings in those valves) is powered by a valve control system. The components of the valve control system include a plunger 50 attached to the perimeter of rotating ring 46. The plunger 50 is pushed by hydraulic fluid through a 180 degree arc toward the far end of a spiral (or helically-shaped) chamber disposed about the circumference of the cylindrically-shaped body of venous anastomotic valve 14. The plunger 50 is connected to a rod 54 (best shown in FIGS. 4A-4C and 5A-5B), which extends through a slot 56 (best shown in FIG. 6) on the interior-facing side of the spiral chamber 52 and attached to a fix point on the perimeter of the rotating ring 46. Thus, when the plunger 50 moves, so does the rotating ring 46. It should be noted that, in the embodiment of the invention shown in FIG. 2, there is only one plunger 50 in the spiral chamber 52 (although multiple plungers may also be used without departing from the scope of the invention). Thus, the illustration in FIG. 2 should not be construed to show five different plungers. Rather, FIG. 2 is meant to show the single plunger 50 as it passes though five different locations in spiral chamber 52.

Hydraulic fluid is introduced into the spiral chamber 52 via second flexible tube 28 interposed between venous anastomotic valve 14 and the medial flow control unit 16. The second flexible fluid tube 28 may be physically attached to a bibb 58 on the perimeter of venous anastomotic valve 14, the bibb being in fluid communication with the open end 60 of the spiral chamber 52. The second flexible fluid tube 28 is secured to the bibb 58 by compressing the end of the second flexible tube 28 between the outside of the bibb 58 and a clamp or rubber band, similar to the method used to fasten and hold second flexible shunt 20 to the tapered end 39 of the venous anastomotic valve 14.

Figure 3A:
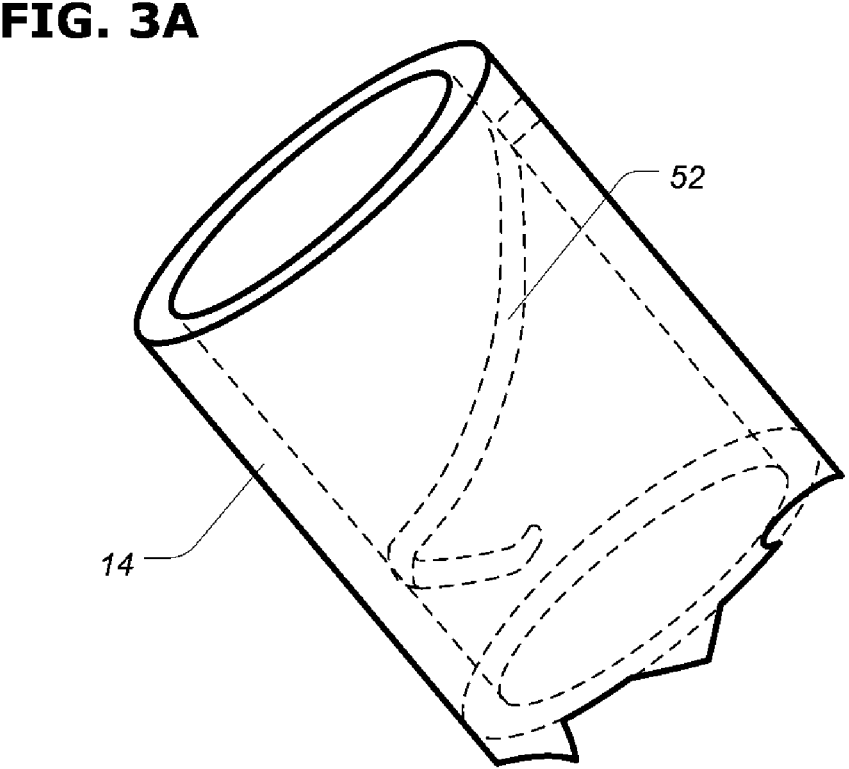
FIGS. 3A and 3B illustrate two examples of the configuration of the spiral chambers in the anastomotic valves according to embodiments of the invention.
Figure 3B:
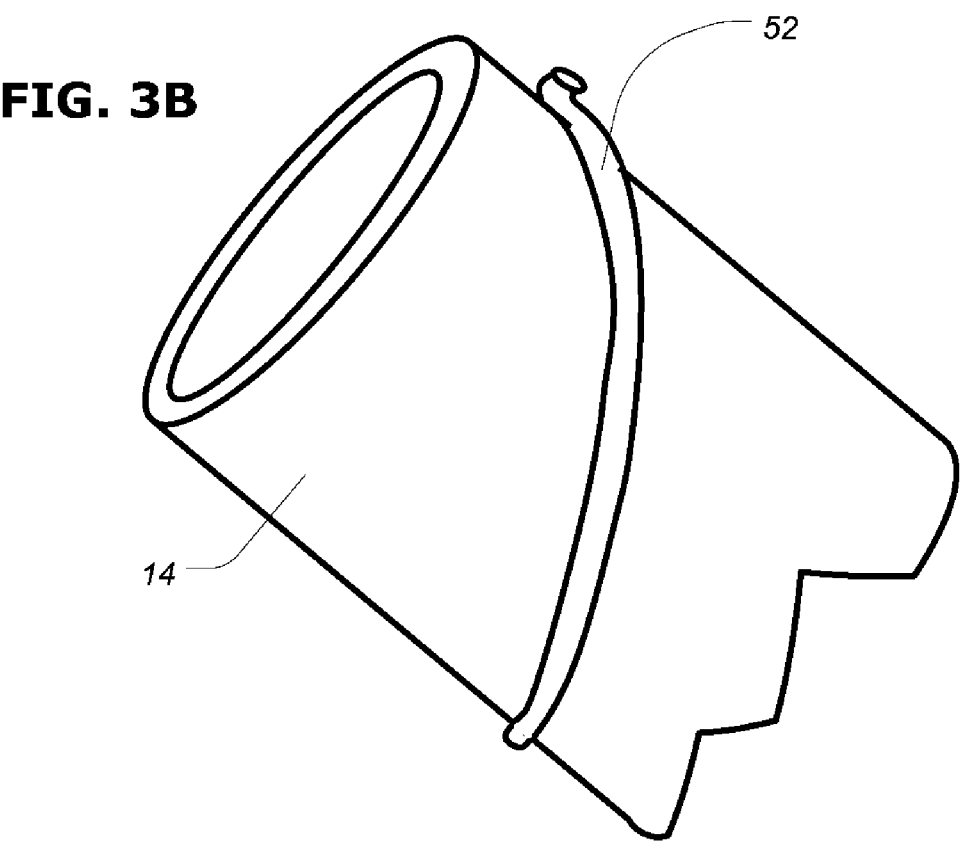

The spiral chamber 52 may be located completely inside the venous anastomotic valve 14 (as best shown in FIGS. 2 and 3A). However, it may also be located wholly or partially outside the exterior wall of venous anastomotic valve 14 (as best shown in FIG. 3B). The end of the spiral chamber 52 opposite from the open end 60 is closed. However, between the closed end 64 and the plunger 50, there is provided a means for biasing the plunger toward the open end 60. The biasing means, which may comprise, for example, a helical metal spring, a gas spring, a compressible foam material, a compressible fluid, or some combination of two or more of these biasing structures, keeps venous anastomotic valve closed when no dialysis session is in progress. In the exemplary embodiment shown in the figures, the biasing means comprises a spiral spring 66 (See FIGS. 4A-4C).

FIGS. 4A, 4B, and 4C show, respectively, cross-sectional views of the venous anastomotic valve 14 in the closed, half open and fully-open positions. In this case, the biasing means comprises a spiral (or helical) spring 66 placed at the closed end 64 of the spiral chamber 52. As shown by these figures, when a sufficient quantity of hydraulic fluid is pushed into the spiral chamber 52 through its open end 60, the plunger 50 is forced to move (in a counterclockwise direction) about 180 degrees around the circumference of the venous anastomotic valve 14, the movement of the plunger being dictated by the spiral chamber 52 in which it is enclosed. This movement causes the rotating ring 46 to rotate 180 degrees counterclockwise; thereby opening the aperture 68 formed by the walls of the cylindrically-shaped sleeve 48, and compressing the spiral spring 66 in the closed end 64 of the spiral chamber 52. (See FIGS. 4B and 4C). While the spiral chamber 52 remains full of hydraulic fluid, the anastomotic valves remain open, which permits blood to flow through the arterial and venous anastomotic valves 12 and 14, the first and second flexible shunts 18 and 20, and the medial flow control unit 16, which provides hemodialysis technicians with access to the flow of blood in the shunts 18 and 20 for dialysis. When the dialysis is completed, the hydraulic fluid is evacuated from the spiral chamber 52 and the spiral spring 66 compressed against the closed end 64 of the spiral chamber 52 begins to decompress and exert sufficient force on the plunger 50 to move the plunger 50 back around the circumference of the venous anastomotic valve 14 in a clock-wise direction, thereby causing the rotating ring 46 to rotate in a clock-wise direction toward its original position. This rotation causes the aperture 68 formed by the walls of the sleeve 48 to contract and close, which cuts off the blood flow. (See FIG. 4A).

Figure 5A:
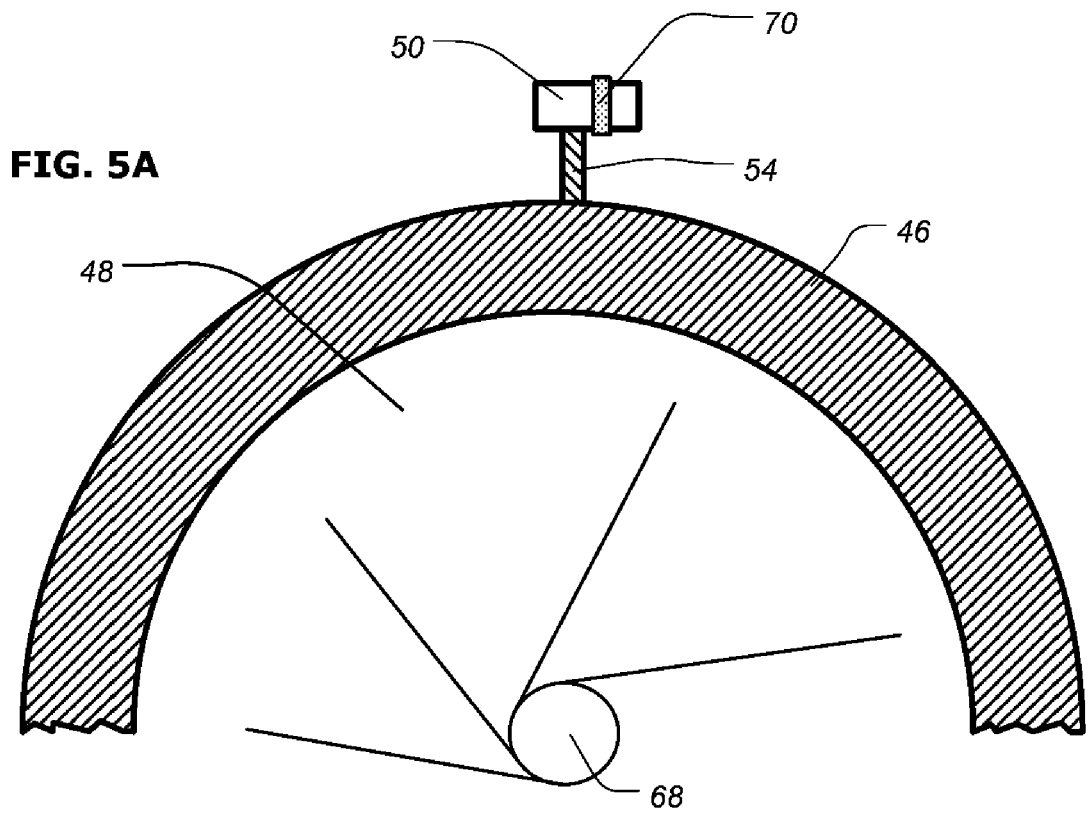
FIGS. 5A, 5B and 6 contain cross-sectional diagrams illustrating the arrangement of the rotating ring, sleeve, rod, slot and plunger in an exemplary embodiment of the invention.
Figure 5B:
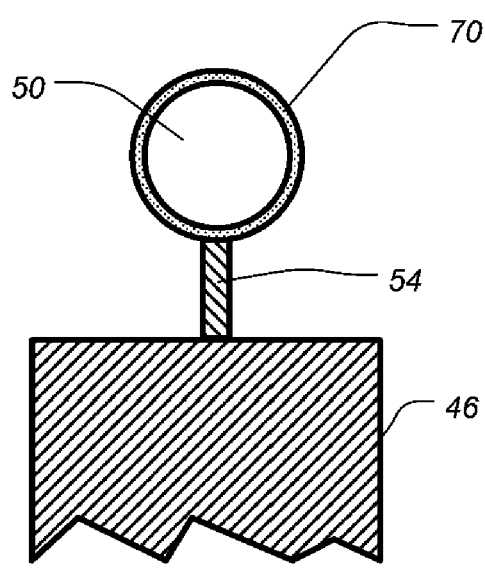
Figure 6:
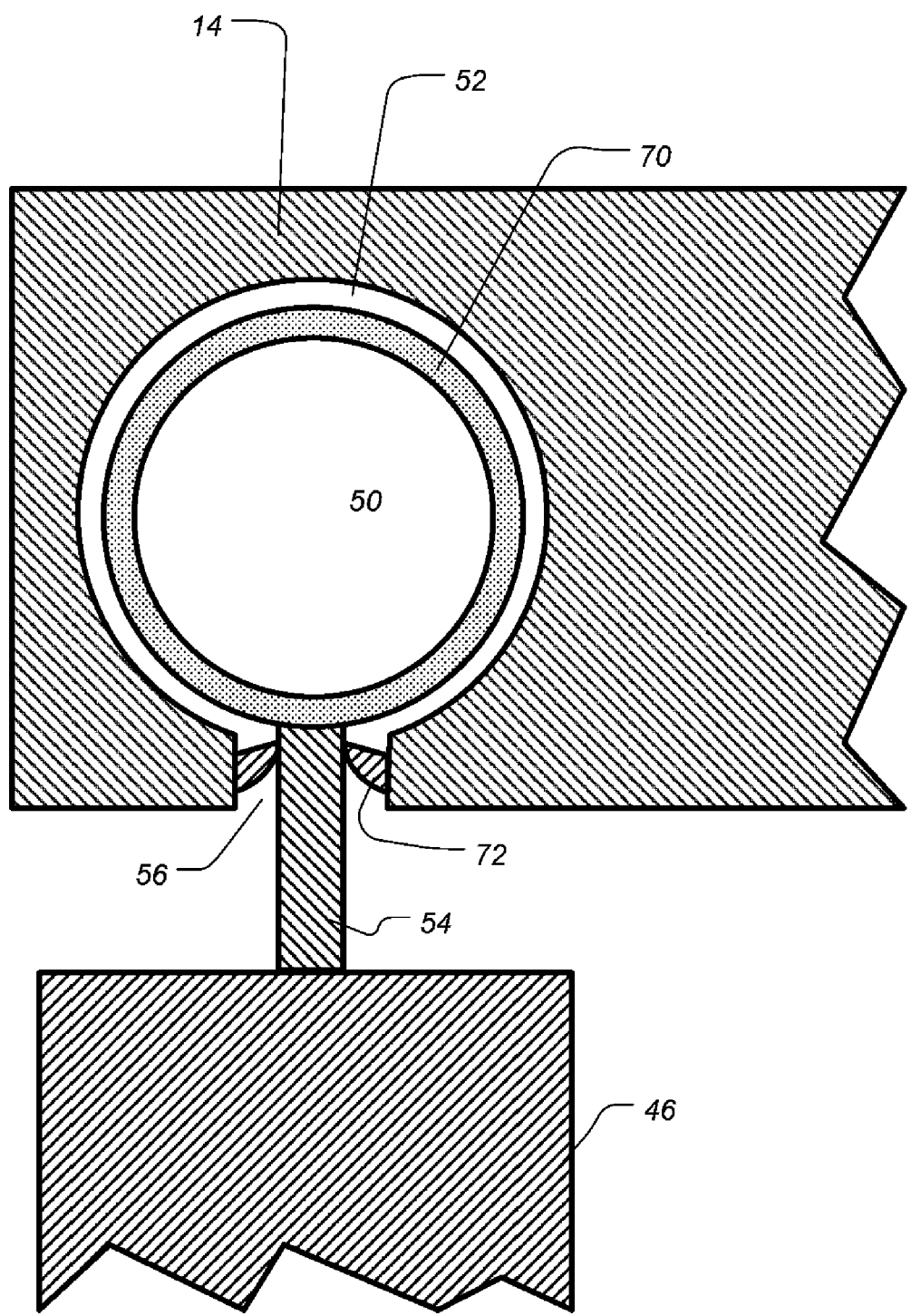

FIGS. 5A, 5B and 6 contain cross-sectional diagrams illustrating the arrangement of the rotating ring 46, sleeve 48, rod 54, slot 56 and plunger. As shown in these figures, the plunger 50 may be fitted with a gasket 70 in order to reduce and/or limit the volume of hydraulic fluid that can squeeze between the plunger 50 and the interior walls of spiral chamber 52 to escape the spiral chamber 52 through the open end 60. Slot 56 may also be fitted with gaskets, flanges and/or bristles 72 in order to prevent hydraulic fluid from escaping the spiral chamber 52 by squeezing through the spaces between the rod 54 and the walls of the slot 56.

It should be noted that the configuration and operation of the arterial anastomotic valve (not shown in the figures) is substantially the same as the configuration and operation of the venous anastomotic valve, except that the blood flows are reversed.

Medial Flow Control Unit (MFCU)

Figure 7:
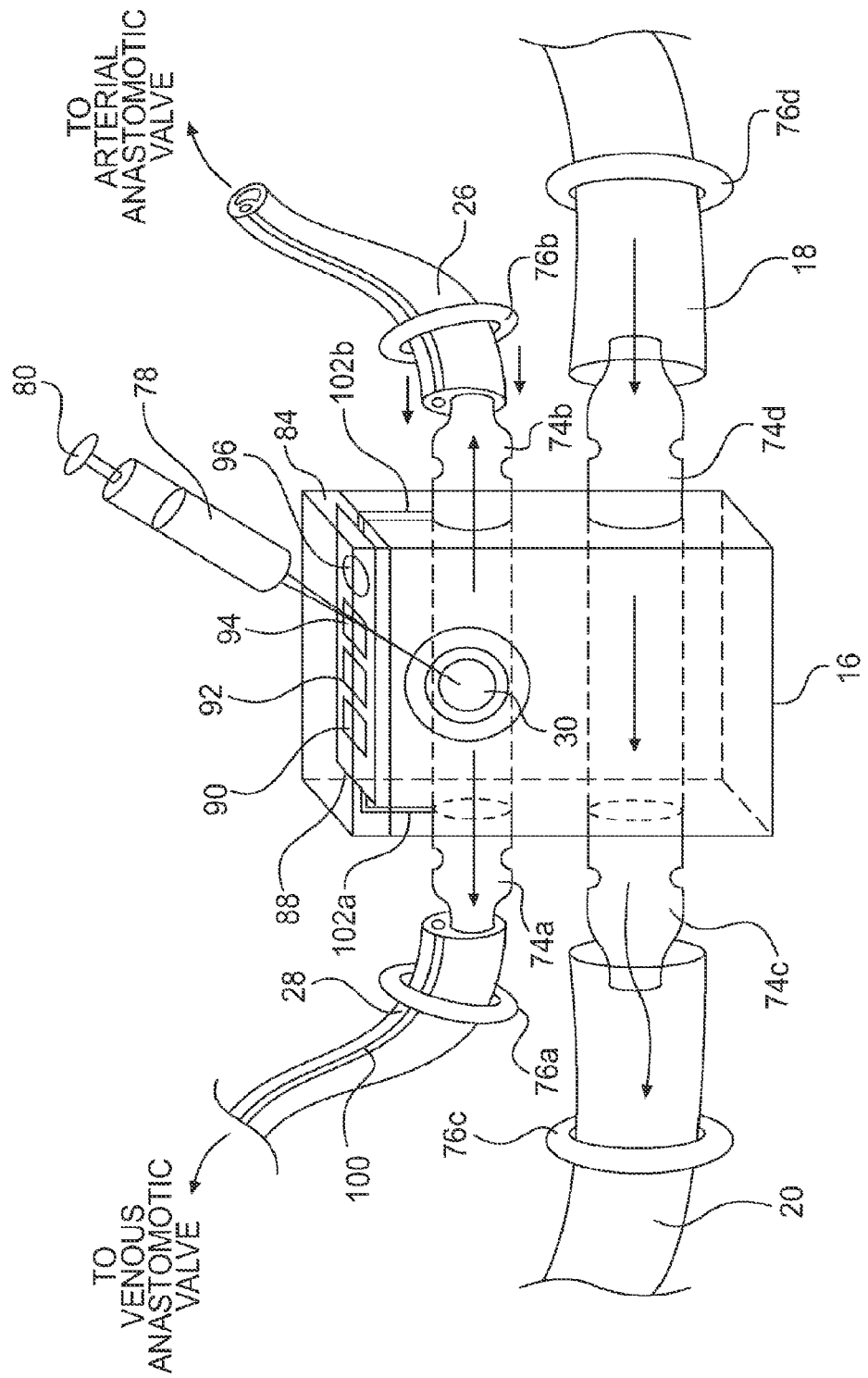
FIG. 7 shows a more detailed view of the medial flow control unit in embodiments of the invention.

FIG. 7 shows a more detailed view of the medial flow control unit 16. As shown in FIG. 7, the ends of the first and second flexible shunts 18 and 20 and the first and second flexible fluid tubes 26 and 28 are connected to bibbs 74a-74d on the medial flow control unit 16 using rubber bands 76a-76d or some other suitable fastener. Preferably, the bibbs 74a-74d are tapered, notched and/or grooved at their distal ends to facilitate sliding them into and securing them to the open ends of the flexible shunts 18 and 20 and flexible fluid tubes 26 and 28 during the implantation procedure. The hydraulic fluid 78 used to move the rotating rings 46 in the arterial and venous anastomotic valves 12 and 14 is introduced into the flexible fluid tubes 26 and 28 via the fluid injection port 30 attached to the medial flow control unit 16. The fluid injection port 30 is in fluid communication with both of the flexible fluid tubes 26 and 28 leading to the spiral chambers 52 in the arterial and venous anastomotic valves 12 and 14.

More specifically, when a hemodialysis session is about to begin, a hypodermic needle 80 is inserted into the fluid injection port 30 on the medial flow control unit 16 to inject a predetermined volume of hydraulic fluid 78 (e.g., saline solution or any other biocompatible solution) into the medial flow control unit 16. The hydraulic fluid 78 is then forced through the bibbs 74a and 74b on the medial flow control unit 16, through the flexible fluid tubes 26 and 28 and into the open ends 60 of the spiral chambers 52 in the arterial and venous anastomotic valves 12 and 14. As previously-stated, this causes the rotating rings in the arterial and venous anastomotic valves 12 and 14 to rotate to their open positions, thereby permitting blood to flow out of the artery 22, into the arterial anastomotic valve 12, through the first flexible shunt 18, through the medial flow control unit 16, through the second flexible shunt 20, through the venous anastomotic valve 14, and finally, out into the vein 24.

Integrated Surveillance System

A major cause of failure associated with AV shunt devices is arterial steal, thrombosis of the venous anastomosis and chronic draining of the vein. To reduce and mitigate these problems, embodiments of the present invention include an integrated surveillance system configured to provide quantitative measurements of blood flow through the vessels in the vicinity of the arterial and venous anastomotic valves 12 and 14. More specifically, the beveled and flanged end of venous anastomotic valve 12 is equipped with one or more flow sensors 82a and 82b (best illustrated in FIG. 2), which are electrically coupled to a processor compartment 84 in the medial flow control unit 16 that houses a printed circuit board 88 (PCB) containing one or more microprocessors 90, memory modules 92, transceivers 94 and batteries 96. These components all operate together to collect, store and wirelessly transmit blood flow data to an external receiver (not shown in FIG. 7).

While it is not the only way, one way of measuring blood flow involves using microelectromechanical systems (MEMS). MEMS fluid anemometers, for example, are capable of measuring the flow of blood based on the rate of heat loss from a heated thermal sensing element to the surrounding blood as it moves pass the element. A voltage applied across the thermal sensing element causes its temperature to increase as the current increases. In the blood flow, the blood absorbs the heat from the sensor by convection, thereby lowering the temperature of the sensor element and resulting in a decreased electrical resistance. Therefore, the voltage drop across the powered resistor can be used to define a parameter which correlates to the flow of blood.

Returning to the venous anastomotic valve diagram of FIG. 2, it can be seen that two MEMS thermal sensing elements 82a and 82b are coupled to the beveled edge of the venous anastomotic valve 14 so that they extend part-way into the path of the blood 38 flowing through the vein 24. FIG. 2 also shows how electrical wire leads 98a and 98b, embedded in the body of the venous anastomotic valve 14, provide electrical connectivity between the MEMS thermal sensing elements 82a and 82b and the bibb 58 (preferably manufactured from a MRI-compatible metal, such as titanium) to which the flexible fluid tube 28 is attached. Each flexible fluid tube 26 and 28 has embedded within it, one or more insulated electrical leads 100 that provide electrical connectivity between the bibb 58 on the venous anastomotic valve 14 and the bibb 74a on the medial flow control unit 16. As shown in FIG. 7, the medial flow control unit 16 is equipped with another set of electrical leads 102a and 102b, which electrically couple bibbs 74a and 74b with the printed circuit board 88 located within the processor compartment 84. The electrical leads 98a, 98b, 102a and 102b are used to transmit low voltage data signals from the MEMs thermal sensors 82a and 82b in the arterial and venous anastomotic valves 12 and 14 to the microprocessor 90, which stores the data in the one or more memory modules 92 using known digital or analog data storage techniques.

Although not shown in the figures, the arterial anastomotic valve 12 may also be equipped with MEMS thermal sensing elements and electrical leads, so that blood flow measurements may also be collected from the areas in the artery adjacent to the arterial anastomotic valve and stored by the microprocessor in the one or more memory modules 90 on the printed circuit board 88.

A transceiver 94 on the printed circuit board is linked to the microprocessor 90. When the transceiver 94 receives a predetermined radio frequency signal from an external transmitter (not shown in FIG. 7), the microprocessor is configured (using well-known microprocessor programming techniques) to retrieve the blood flow data from the one or more memory modules 92 and then cause the transceiver 94 to wirelessly transmit the retrieved blood flow data to an external receiver. See, for example, U.S. Pat. No. 6,434,429, the disclosure of which is incorporated herein by reference, for a more detailed discussion of known close- and long-range telemetry techniques for implantable devices.

Although the exemplary embodiments of the invention have been disclosed above with a certain degree of particularity, it will be apparent to those skilled in the art upon consideration of this specification and practice of the invention as disclosed herein that alterations and modifications can be made without departing from the spirit or the scope of the invention.

What is claimed is:

1. A modular arteriovenous shunt device, comprising:
   three or more conjoined pieces connected in a series, the three or more conjoined pieces comprising a first flexible shunt, a second flexible shunt, and a medial flow control unit interposed between said first flexible shunt and said second flexible shunt;
   an arterial anastomotic valve that permits blood flowing through an artery to pass into the three or more conjoined pieces;
   a venous anastomotic valve that permits blood flowing through the three or more conjoined pieces to pass into a vein;
   a valve control system to control (i) the rate at which blood is permitted to enter the three or more conjoined pieces via the arterial anastomotic valve, and (ii) the rate at which blood is permitted to exit the three or more conjoined pieces via the venous anastomotic valve; and
   an integrated surveillance system that automatically generates and stores flow data representing the flow of blood through at least one of said vein and artery.

2. The modular arteriovenous shunt device of claim 1, wherein
   said arterial anastomotic valve comprises a first static ring, a first rotating ring, and an arterial aperture formed by a first cylindrical sleeve fixedly attached at each end to said first static ring and said first rotating ring; and
   said venous anastomotic valve comprises a second static ring, a second rotating ring, and a venous aperture formed by a second cylindrical sleeve fixedly attached at each end to said second static ring and said second rotating ring;
   whereby rotating the first and second rotating rings in a first direction causes the first and second cylindrical sleeves to untwist, thereby expanding the arterial and venous apertures to increase the rate blood is permitted to flow therethrough, and rotating the first and second rotating rings in an opposite direction causes the first and second cylindrical sleeves to twist, thereby contracting the arterial and venous apertures to reduce the rate blood is permitted to flow therethrough.

3. The modular arteriovenous shunt device of claim 2, wherein the valve control system comprises:
   a first spiral chamber disposed about the circumference of the arterial anastomotic valve, the first spiral chamber having an open end, a closed end and a slot running along its interior-facing side;
   a plunger slidably enclosed in the first spiral chamber;
   means for biasing the plunger toward the open end;
   a rod extending through the slot, the rod having one end connected to the plunger and the other end connected to a fixed position on the perimeter of the first rotating ring;
   a fluid injection port attached to the medial flow control unit; and
   a first flexible fluid tube in fluid communication with both the fluid injection port and the open end of the first spiral chamber, said first flexible fluid tube being at least partially filled with hydraulic fluid;
   whereby injecting additional hydraulic fluid into said fluid injection port causes the hydraulic fluid inside said first flexible tube to pass into said first spiral chamber, thereby forcing the plunger to move toward the closed end of said first spiral chamber, which causes said first rotating ring to rotate in said first direction to expand said arterial aperture.

4. The modular arteriovenous shunt device of claim 3, wherein extracting said additional hydraulic fluid from said fluid injection port causes said hydraulic fluid to evacuate said first spiral chamber, which permits the biasing means to force the plunger toward the open end of said first spiral chamber, thereby causing said first rotating ring to rotate in said opposite direction to contract the arterial aperture.

5. The modular arteriovenous shunt device of claim 4, wherein the biasing means comprises one of the following:
   a spiral spring;
   a gas spring;
   a compressible foam; and
   a compressible fluid.

6. The modular arteriovenous shunt device of claim 5, wherein the valve control system further comprises:
   a second spiral chamber disposed about the circumference of the venous anastomotic valve, the second spiral chamber having a second open end, a second closed end and a second slot running along its interior-facing side;
   a second plunger slidably enclosed in the second spiral chamber;
   a second means for biasing the second plunger toward said second open end;
   a second rod extending through the second slot, the second rod having one end connected to the second plunger and the other end connected to a fixed position on the perimeter of the second rotating ring; and
   a second flexible fluid tube in fluid communication with both the fluid injection port and the second open end, said second flexible fluid tube being at least partially filled with hydraulic fluid;
   whereby injecting the additional hydraulic fluid into said fluid injection port also causes the hydraulic fluid inside said second flexible tube to pass into said second spiral chamber, thereby forcing the second plunger to move toward the closed end of said second spiral chamber, which causes said second rotating ring to rotate in said first direction to expand said venous aperture.

7. The modular arteriovenous shunt device of claim 6, wherein extracting said additional hydraulic fluid from said fluid injection port causes said hydraulic fluid to evacuate said second spiral chamber, which permits the second biasing means to force the second plunger toward the second open end of said second spiral chamber, thereby causing said second rotating ring to rotate in said opposite direction to contract the venous aperture.

8. The modular arteriovenous shunt device of claim 5, wherein the second biasing means comprises one of the following:
   a second spiral spring;

a second gas spring;
a second compressible foam; and
a second compressible fluid.

9. The modular arteriovenous shunt device of claim 1, wherein said integrated surveillance system comprises:
   a venous flow sensor attached to the venous anastomotic valve; and
   an electrical lead electrically coupling the venous flow sensor to the medial flow control unit;
   wherein the venous flow sensor is configured to generate the flow data by measuring the flow of blood in the vicinity of the venous anastomotic valve and transmit the flow data to the medial flow control unit via the electrical lead.

10. The modular arteriovenous shunt system of claim 9, wherein the venous flow sensor comprises a hot-wire anemometer configured to measure the forced convective heat transfer from a thermal element to the blood.

11. The modular arteriovenous shunt device of claim 10, wherein the integrated surveillance system further comprises:
   a memory; and
   a microprocessor configured to store the flow data in the memory.

12. The modular arteriovenous shunt device of claim 11, further comprising:
   a transceiver, coupled to the microprocessor, which receives a radio frequency signal generated by an external transmitter;
   wherein, responsive to the receipt of the radio signal, the microprocessor will retrieve the flow data from the memory and cause the transceiver to transmit the flow data to an external receiver.

13. The modular arteriovenous shunt device of claim 11, wherein the medial flow control unit further comprises a power source.

14. The modular arteriovenous shunt device of claim 1, wherein the integrated surveillance system comprises:
   an arterial flow sensor attached to the arterial anastomotic valve; and
   an electrical lead electrically coupling the arterial flow sensor to the medial flow control unit;
   wherein the arterial flow sensor is configured to generate the flow data by measuring the flow of blood in the vicinity of the arterial anastomotic valve and to transmit the flow data to the medial flow control unit via the electrical lead.

15. The modular arteriovenous shunt system of claim 14, wherein the arterial flow sensor comprises a hot-wire anemometer configured to measure the forced convective heat transfer from a thermal element to the blood.

16. The modular arteriovenous shunt device of claim 14, wherein the medial flow control unit comprises:
   a memory; and
   a microprocessor configured to store the flow data in the memory.

17. The modular arteriovenous shunt system of claim 16, further comprising:
   a transceiver, coupled to the microprocessor, which receives a radio frequency signal generated by an external transmitter;
   wherein, responsive to the receipt of the radio signal, the microprocessor will retrieve the flow data from the memory and cause the transceiver to transmit the flow data to an external receiver.

18. The modular arteriovenous shunt device of claim 16, wherein the medial flow control unit further comprises a power source.

19. The modular arteriovenous shunt system of claim 1, wherein said integrated surveillance system automatically generates and stores said flow data while said arterial anastomotic valve and said venous anastomotic valves are closed.

20. The modular arteriovenous shunt system of claim 1, wherein said integrated surveillance system automatically generates and stores said flow data while said arterial anastomotic valve and said venous anastomotic valves are open.

21. A method of establishing hemodialytic angioaccess in a patient, comprising:
   attaching an arterial anastomotic valve to an artery, the arterial anastomotic valve comprising a first static ring, a first rotating ring, and an arterial aperture formed by a first sleeve interposed between the first static ring and the first rotating ring;
   attaching a venous anastomotic valve to a vein, the venous anastomotic valve comprising a second static ring, a second rotating ring, and a venous aperture formed by a second sleeve interposed between the second static ring and the second rotating ring;
   providing a medial flow control unit;
   installing a first flexible shunt between the medial flow control unit and the arterial anastomotic valve;
   installing a second flexible shunt between the medial flow control unit and the venous anastomotic valve; and
   rotating the first and second rotating rings in a first direction to cause the first and second sleeves to untwist, thereby expanding the arterial and venous apertures to increase the rate at which blood is permitted to flow through the arterial and venous anastomotic valves.

22. The method of claim 21, further comprising rotating the first and second rotating rings in an opposite direction to the first and second sleeves to twist, thereby contracting the arterial and venous apertures to reduce the rate at which blood is permitted to flow through the arterial and venous anastomotic valves.

23. The method of claim 22, further comprising:
   installing a first hydraulic fluid tube between the arterial anastomotic valve and the medial flow control unit;
   installing a second hydraulic fluid tube between the venous anastomotic valve and the medial flow control unit;
   at least partially filling said first and second hydraulic fluid tubes with hydraulic fluid; and
   injecting additional hydraulic fluid into the medial flow control unit, thereby forcing the hydraulic fluid in said first and second hydraulic fluid tubes to pass into said arterial and venous anastomotic valves, thereby forcing said first and second rotating rings to rotate in said first direction to expand said arterial and venous apertures.

24. The method of claim 23, further comprising:
   extracting the additional hydraulic fluid from the medial flow control unit, thereby forcing the hydraulic fluid to evacuate said arterial and venous anastomotic valves, thereby causing said first and second rotating rings to rotate in said opposite direction to contract said arterial and venous apertures.

25. The method of claim 21, wherein the venous anastomotic valve comprises a venous flow sensor.

26. The modular arteriovenous shunt system of claim 25, wherein the venous flow sensor comprises a hot-wire anemometer configured to measure the forced convective heat transfer from a thermal element to the blood.

27. The method of claim 25, further comprising:
   electrically coupling the venous flow sensor to the medial flow control unit with an electrical lead; and transmitting data describing the flow of blood in the vicinity of the venous anastomotic valve to the medial flow control unit via the electrical lead.

28. The method of claim 27, wherein the medial flow control unit further comprises:
a memory;
a microprocessor configured to store the data in the memory; and
a transceiver.

29. The method of claim 28, further comprising:
receiving on said transceiver a radio frequency signal generated by an external transmitter; and
responsive to receiving the radio signal, causing the microprocessor to retrieve the data from the memory and the transceiver to transmit the data to an external receiver.

30. The method of claim 21, wherein the arterial anastomotic valve further comprises an arterial flow sensor.

31. The method of claim 30, wherein the arterial flow sensor comprises a hot-wire anemometer configured to measure the forced convective heat transfer from a thermal element to the blood.

32. The method of claim 31, further comprising:
electrically coupling the arterial flow sensor to the medial flow control unit with an electrical lead; and
transmitting data describing the flow of blood in the vicinity of the arterial anastomotic valve to the medial flow control unit via the electrical lead.

33. The method of claim 32, wherein the medial flow control unit comprises:
a memory;
a microprocessor configured to store the data in the memory; and
a transceiver.

34. The method of claim 33, further comprising:
receiving on said transceiver a radio frequency signal generated by an external transmitter; and
responsive to receiving the radio signal, causing the microprocessor to retrieve the data from the memory and the transceiver to transmit the data to an external receiver.

35. A method monitoring the patency of a modular arteriovenous shunt implanted in a hemodialysis patient, the method comprising:
providing a first flexible shunt comprising an arterial anastomotic valve and an first adjustable length end opposite the anastomotic valve;
providing a second flexible shunt comprising a venous anastomotic valve, a second adjustable length end opposite the venous anastomotic valve, and a flow sensor attached to the venous anastomotic valve;
providing a medial flow control unit comprising a memory, a transceiver and a microprocessor linked to the memory and the transceiver;
implanting the arteriovenous shunt in the hemodialysis patient by connecting the arterial anastomotic valve to an artery in the patient, connecting the venous anastomotic valve to a vein in the patient, coupling the first flexible shunt to the second flexible shunt by connecting medial flow control unit to the first and second adjustable length ends of the first and second flexible shunts, and electrically coupling the flow sensor attached to the venous anastomotic valve to the microprocessor in the medial flow control unit;
generating flow data with the flow sensor by causing the flow sensor to periodically measure the flow of blood through the vein in the vicinity of the connection between the vein and the venous anastomotic valve;
storing the flow data in the memory of the medial flow control unit; and
collecting the flow data by transmitting to the medial flow control unit a predetermined radio frequency signal that causes the microprocessor and the transceiver to retrieve the flow data from the memory and transmit the flow data to an external receiver.

36. The method of claim 35, further comprising cutting the first adjustable length end of the first flexible shunt during the implanting step.

37. The method of claim 35, further comprising cutting the second adjustable length end of the second flexible shunt during the implanting step.

38. The method of claim 35, further comprising generating and storing the flow data while the arterial and venous anastomotic valves are closed.

39. The method of claim 35, further comprising generating and storing the flow data while the arterial and venous anastomotic valves are open.

40. The method of claim 35, wherein:
the arterial anastomotic valve comprises a second flow sensor; and
the step of generating the flow data further comprises causing the second flow sensor to periodically measure the flow of blood through the artery in the vicinity of the connection between the artery and the arterial anastomotic valve.

* * * * *

UNITED STATES PATENT AND TRADEMARK OFFICE
CERTIFICATE OF CORRECTION

| | | |
|---|---|---|
| PATENT NO. | : 8,057,421 B2 | |
| APPLICATION NO. | : 12/189669 | |
| DATED | : November 15, 2011 | |
| INVENTOR(S) | : Ajibola George Akingba | |

It is certified that error appears in the above-identified patent and that said Letters Patent is hereby corrected as shown below:

Column 6, line 43, delete "or" and insert --are--;
        line 58, delete the second occurrence of "and";

Column 12, line 50, after "keeps" insert --the--; and

Column 18, lines 61, replace "modular arteriovenous shunt system" with --method--.

Signed and Sealed this
Tenth Day of July, 2012

David J. Kappos
*Director of the United States Patent and Trademark Office*